United States Patent
Schnipke et al.

(10) Patent No.: US 8,291,571 B2
(45) Date of Patent: Oct. 23, 2012

(54) SURGICAL CARTRIDGE WALL EXPANDER

(75) Inventors: Leonard J. Schnipke, Ft. Jennings, OH (US); Brian Doepker, Kalida, OH (US); Ronald J. Schnipke, Cloverdale, OH (US)

(73) Assignee: The Schnipke Family, LLC, Ottoville, OH (US)

( * ) Notice: Subject to any disclaimer, the term of this patent is extended or adjusted under 35 U.S.C. 154(b) by 116 days.

(21) Appl. No.: 12/966,336

(22) Filed: Dec. 13, 2010

(65) Prior Publication Data

US 2011/0078891 A1 Apr. 7, 2011

Related U.S. Application Data

(62) Division of application No. 11/528,859, filed on Sep. 28, 2006, now Pat. No. 7,870,716.

(51) Int. Cl.
*B23Q 3/00* (2006.01)
*A61B 17/04* (2006.01)
*A61B 17/10* (2006.01)

(52) U.S. Cl. ......... 29/464; 29/811.2; 29/466; 29/468; 227/110; 227/176.1

(58) Field of Classification Search ............ 29/464, 29/811.2, 466, 468, 469; 57/71, 77; 264/138, 264/249; 227/110, 120, 176.1; 606/134, 606/144
See application file for complete search history.

(56) References Cited

U.S. PATENT DOCUMENTS

| | | | |
|---|---|---|---|
| 5,018,657 A * | 5/1991 | Pedlick et al. | 227/178.1 |
| 5,653,928 A | 8/1997 | Schnipke | |
| 5,836,147 A | 11/1998 | Schnipke | |
| 6,158,205 A | 12/2000 | Schnipke et al. | |
| 6,729,119 B2 | 5/2004 | Schnipke et al. | |
| 6,973,770 B2 * | 12/2005 | Schnipke et al. | 59/71 |
| 6,990,796 B2 * | 1/2006 | Schnipke et al. | 227/180.1 |
| 7,207,168 B2 * | 4/2007 | Doepker et al. | 59/71 |
| 7,870,716 B2 * | 1/2011 | Schnipke et al. | 59/71 |
| 7,992,755 B2 * | 8/2011 | Kameda | 227/131 |
| 8,056,791 B2 * | 11/2011 | Whitman | 227/180.1 |
| 8,186,559 B1 * | 5/2012 | Whitman | 227/180.1 |

* cited by examiner

*Primary Examiner* — Essama Omgba
(74) *Attorney, Agent, or Firm* — Jason H. Foster; Kremblas & Foster

(57) ABSTRACT

A pocket-sizing method for a device that inserts staple drivers into pockets aligned to form a slot in a surgical staple cartridge. A fin extends from a driver guide fixture for insertion into the slot. The fin increases the size of the slot, thereby aiding in inserting drivers into the pockets. Preferably a second fin extends from the driver guide fixture adjacent the fixture passage and aligned with the first fin. A gap is formed between the first and second fins, extending from a first edge to an opposite edge of the fixture passage. The driver is driven through the gap. The fins are substantially equal to the thickness of the driver. The fins have tapered leading edges to aid cartridge insertion and removal, and a lip extends from the driver guide fixture for preventing the fins from widening the slot too much and for narrowing an overly wide slot.

4 Claims, 15 Drawing Sheets

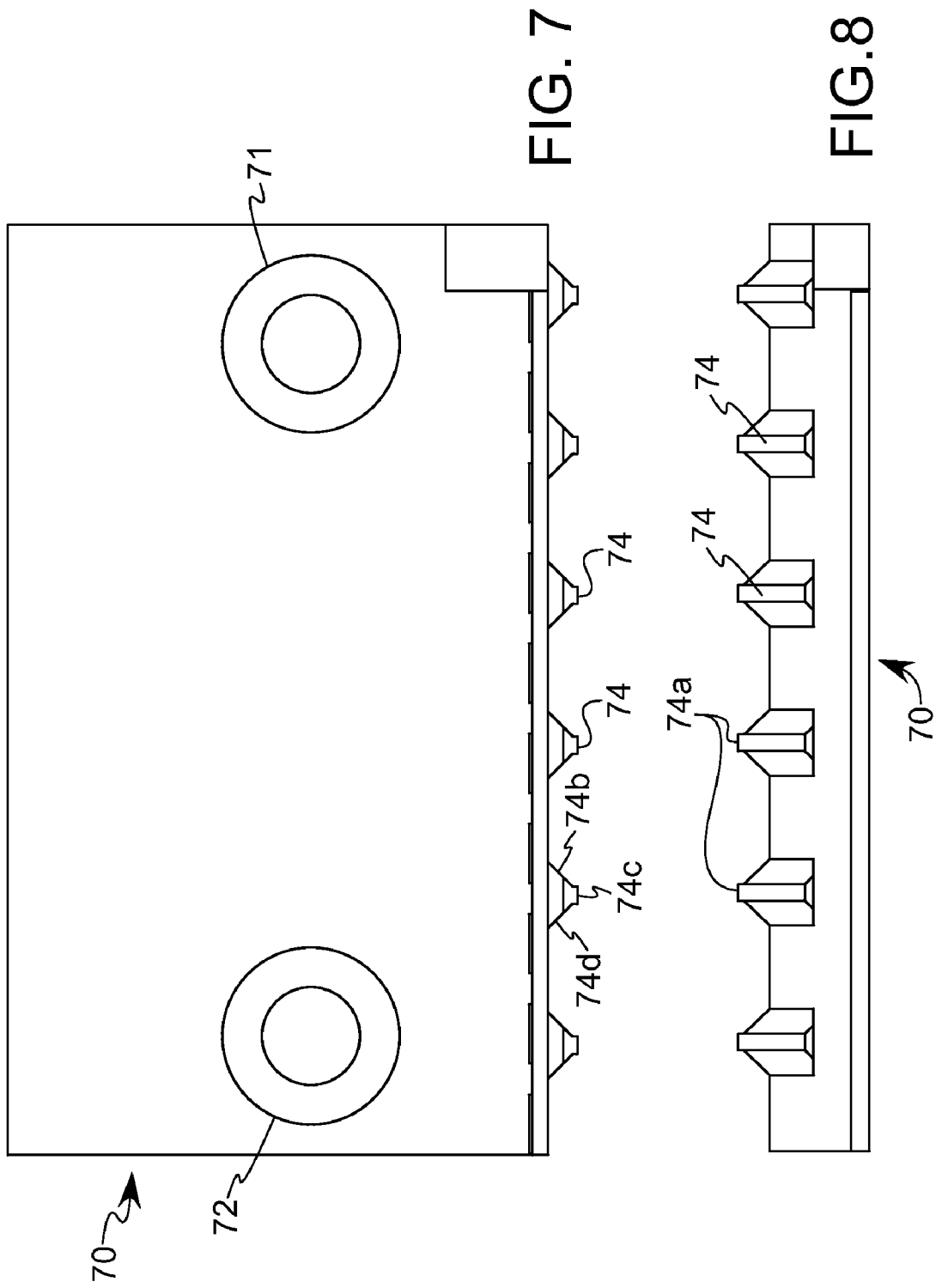

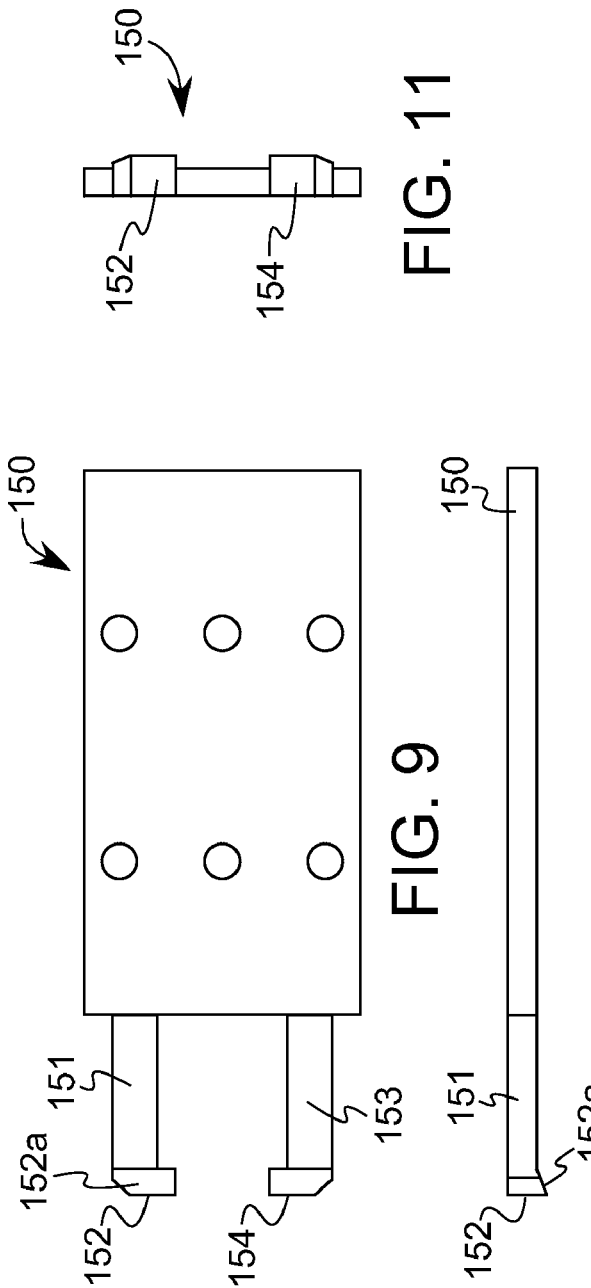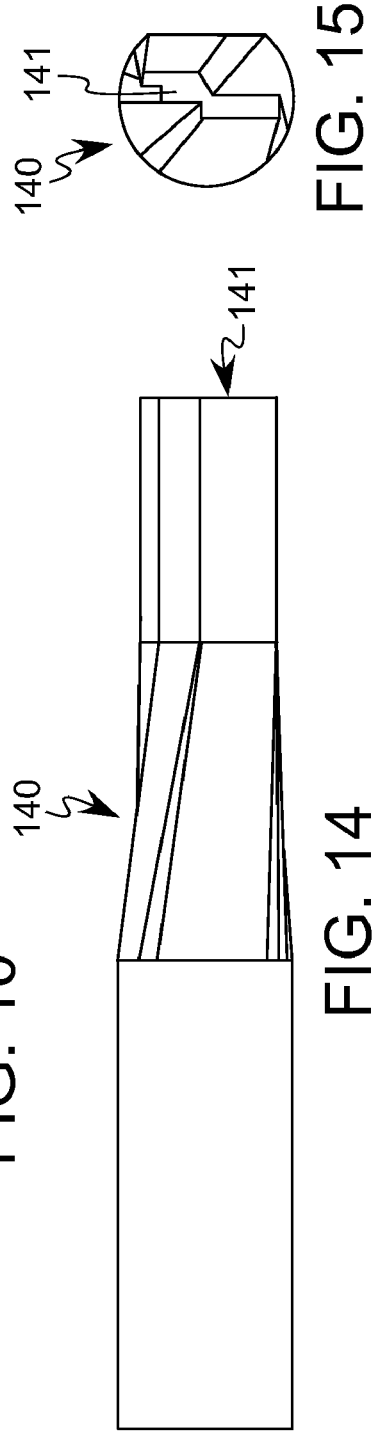

SURGICAL CARTRIDGE WALL EXPANDER

CROSS-REFERENCES TO RELATED APPLICATIONS

This is a divisional of U.S. application Ser. No. 11/528,859, filed Sep. 28, 2006, which is incorporated herein by reference, and is now U.S. Pat. No. 7,870,716 issued Jan. 18, 2011.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

The present invention relates generally to an apparatus and a method for inserting discrete articles into surgical cartridges, and more particularly relates to an improved device and method for inserting staple drivers into surgical stapling cartridges.

2. Description of the Related Art

In the field of microsurgery, a surgical instrument having a cutting blade traverses a specific path through tissue. One feature of the surgical instrument is a single-use cartridge that is a holder for surgical staples. The cartridge is an elongated plastic body with a longitudinal channel that serves as a guide for a surgical blade. The cartridge has rows of small staples on opposite sides of the channel, and these rows are aligned parallel to the guide channel. Drivers are inserted in apertures (also called "pockets") aligned with the rows in order to push the staples out of the cartridge and through the adjacent tissue. Before the blade has made its cut, each side of the incision is stapled together by displacing the drivers relative to the cartridge. This displacement forces the staples against an anvil on the opposing side of the surgical instrument as the cartridge and the anvil deflects the points of the staples into a clasping position.

There may be as many as fifty or more very small staples on each side of a two inch incision. Each staple can be driven simultaneously into the tissue to close the incision by the correspondingly small drivers. The task of inserting the drivers into the cartridge is labor-intensive due to the small size of the drivers.

One prior art system for holding the very small staple drivers before and during mounting in the cartridge pockets includes a plastic holder that is referred to as a "tree." There are multiple aligned "branches" on the tree, and a driver is mounted to the end of each branch, such as integrally molding the driver to the branch. During installation of the drivers, the cartridge is placed in a holding apparatus, and the tree is hand-manipulated to place a driver at the entrance to each pocket, or at least at the entrance to as many pockets as there are drivers on the tree. This is normally accomplished by inserting each driver into a funnel-shaped passage that is aligned with a pocket. Each driver is subsequently separated from its respective branch and driven into the associated pocket of the cartridge. The separation of the drivers from the branches of the tree is accomplished by flexing the branches of the tree manually to fracture the joint between the driver and the branch. Then, a hand-manipulated tool is used to press each driver down into the cartridge pocket to near the pocket opening on the opposite side of the cartridge as the pocket entrance.

The operation of manually aligning each driver with a pocket, flexing the branches and pressing from the hand-operated tool can misalign the drivers relative to the axes of the respective pockets. The drivers are inserted into the funnel-shaped passages on the fixture so as to align each individual driver with an associated pocket on the cartridge. However, the funnel-shaped passages do not fully cure the misalignment problem, because the funnels do not fully engage the driver to be inserted.

If the driver is not properly aligned within the pocket, the staple which is ejected by displacement of the staple driver may be inaccurately bent during the surgery. In addition, the misalignment of the staple driver in the pocket can increase the force needed to eject a staple or prevent the ejection of that staple entirely.

An additional potential problem arises due to slight variations in the sizes of the pockets and the drivers due to the minute structure involved and the fact that both the cartridge and the staple drivers are formed of thermoplastic resin, which cools from a liquid or semi-liquid with imperfect and irregular shrinkage. This combination of factors can create gaps between the components, which can exacerbate alignment problems. Additionally, inversion of the cartridge after assembly can result in some of the drivers falling out of their pockets. If a staple driver is absent, no staple will be driven into the tissue at that point in the incision, which increases the chances of surgical complications.

Yet another problem is the imprecision in the process of separating the staple drivers from the branches of the plastic "tree", a process referred to as "degating." The drivers are mounted to the tree prior to their insertion in the pockets, and must be removed from the tree before or during the insertion process. The separation of a driver from the tree is not precise, and therefore it leaves a remnant of material on one side of each driver. The remnants of material left on the drivers are not a predictable size, and often the remnants are larger than desired. While it is not practical to remove all of the "branch" material from the side of each driver in the separation process, it is important that the amount of material left on each driver be relatively consistent between drivers. This is because the material left on the side tends to cause friction when the staple driver is used in surgery. If the amount of material left is consistent, it allows a user of the staple cartridge to accurately predict the amount of force needed to expel the staples during surgery. In addition, the smaller the volume of material left, the less friction will be generated, and the less the force required to use the staple cartridge.

It is known in the prior art to insert drivers mechanically into surgical stapling cartridges, as shown in U.S. Pat. No. 5,836,147 to Schnipke, U.S. Pat. No. 5,653,928 to Schnipke, and U.S. Pat. No. 6,158,205 to Schnipke et al., all of which are incorporated herein by reference. These patents show machines that require people to position the cartridges and the holders that contain the drivers relative to the machine, and then actuate the machine to insert the tiny drivers into the pockets in the cartridges. After a fraction of the total number of drivers is inserted by one machine, the cartridge is then manually transported to the next machine, which inserts another fraction of the drivers.

If a driver is improperly inserted into a cartridge, or is omitted, the cartridge is either discarded or repaired. Thus, errors in insertion of the tiny parts can result in wasted time and/or product.

Even the machines disclosed and claimed in the patents referenced above, although representing a significant improvement over the prior art, have problems, especially with the pockets collapsing slightly during cooling. These collapsed pockets either prevent drivers from being driven into them or damage the drivers that are driven into them as a result of scraping.

In U.S. Pat. No. 6,729,119 to Schnipke et al., which is incorporated herein by reference, a robotic loader is discussed for use in filling the cartridges discussed herein. However, this patent does not address the problems that continue to exist on the non-robotic devices discussed above.

Therefore, there is a need for an improved machine for loading drivers into surgical cartridges.

BRIEF SUMMARY OF THE INVENTION

The invention is a pocket-sizing apparatus for a device that inserts staple drivers into pockets aligned to form a slot in a surgical staple cartridge. The device that inserts staple drivers includes a cartridge-receiving plate having a channel configured to receive a cartridge. A driver guide fixture is mounted adjacent the channel with a fixture passage that receives and guides the driver into the pocket. A cutter is mounted with at least one sharp edge adjacent the fixture passage and a plunger is aligned with the fixture passage for forcing the driver toward the fixture passage. The pocket-sizing apparatus comprises a first fin extending from the driver guide fixture adjacent the fixture passage toward the channel for insertion into said slot on the cartridge. The fin can increase the size of the slot if the slot is smaller than a desired width, thereby aiding in inserting drivers into the pockets that align to form the slot.

It is preferred that a second fin extends from the driver guide fixture adjacent the fixture passage and aligned with the first fin for insertion into the slot on the cartridge. A gap is preferably formed between the first and second fins, and the gap extends at least from a first edge of the fixture passage to an opposite edge of the fixture passage. The driver is driven through the gap and into the pocket of the cartridge. The thickness of the fins is preferably substantially equal to the thickness of the driver in order to widen a too-narrow slot to substantially the same width as the driver. Preferably the fins have tapered leading edges to ease the fins into and out of the slot. In a most preferred embodiment, a lip extends from the driver guide fixture, is spaced from, and is substantially parallel to, the first and second fins, for seating against the cartridge. The lip prevents the fins from widening the slot too much and also will narrow an overly wide slot.

BRIEF DESCRIPTION OF THE SEVERAL VIEWS OF THE DRAWINGS

FIG. 7 is a top view illustrating the preferred cutter of FIG. 6.

FIG. 8 is a side view illustrating the preferred cutter of FIG. 6.

FIG. 9 is an end view illustrating the preferred cartridge-locator plate.

FIG. 10 is a side view illustrating the preferred cartridge-locator plate of FIG. 9.

FIG. 11 is a top view illustrating the preferred cartridge-locator plate of FIG. 9.

FIG. 14 is a side view illustrating a preferred pin.

FIG. 15 is a bottom view illustrating a preferred pin.

Figure 1:
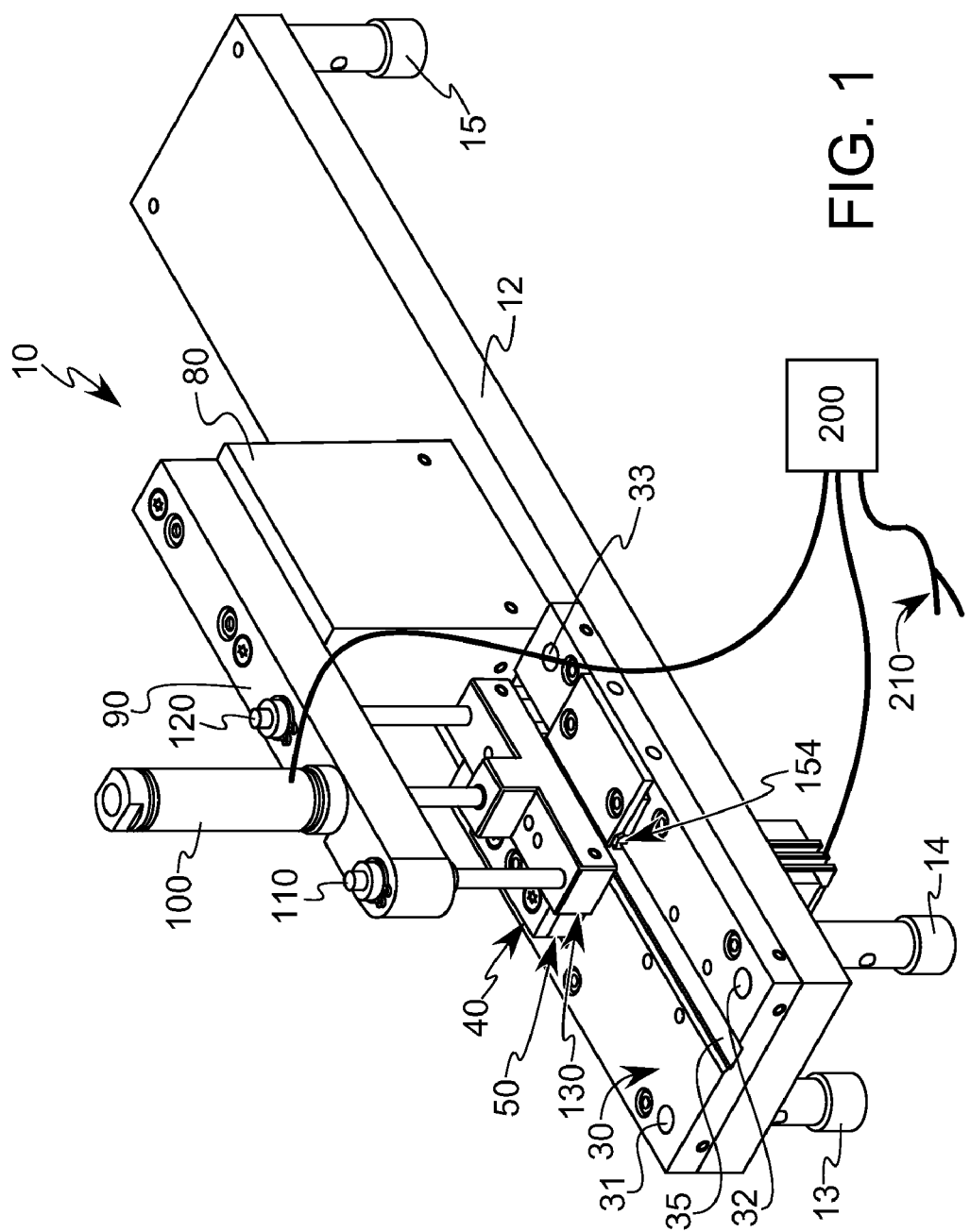
FIG. 1 is a view in perspective illustrating a preferred embodiment of the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

The preferred staple driver insertion machine 10 is shown in FIG. 1 having a base 12 with four supporting legs 13, 14, 15 and 16 extending downwardly therefrom (leg 16 is not visible in FIG. 1, but is identical to the other legs and is located at the base's fourth corner). The supporting legs 13-16 are not essential, and can be replaced by other suitable support structures. When the machine 10 is in use, the legs are preferably seated at their lower ends against the upwardly facing surface of a table or workbench so that a worker can sit in front of the machine 10 while operating the same as described herein.

Figure 2:
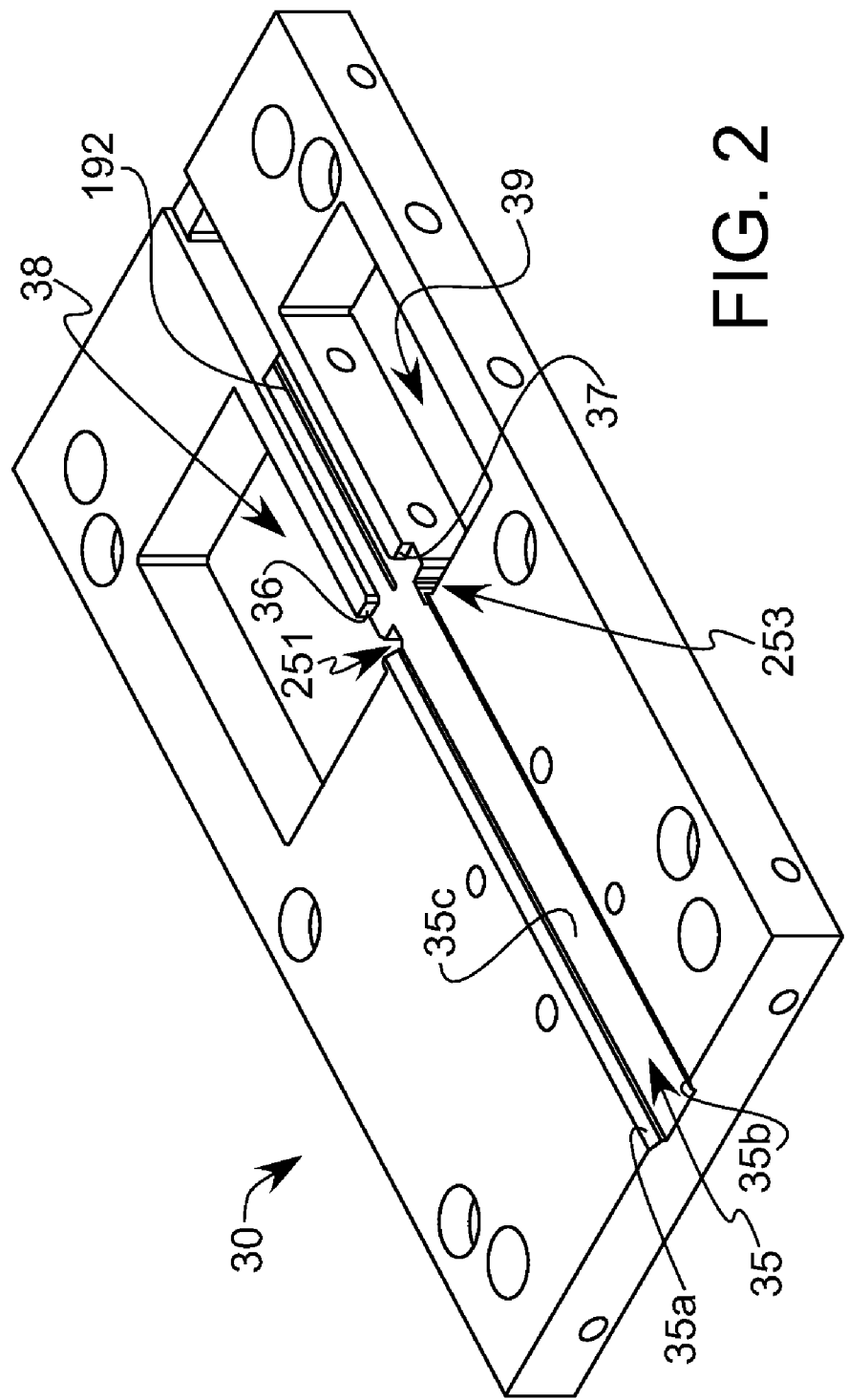
FIG. 2 is a view in perspective illustrating a preferred component of the present invention.
Figure 13:
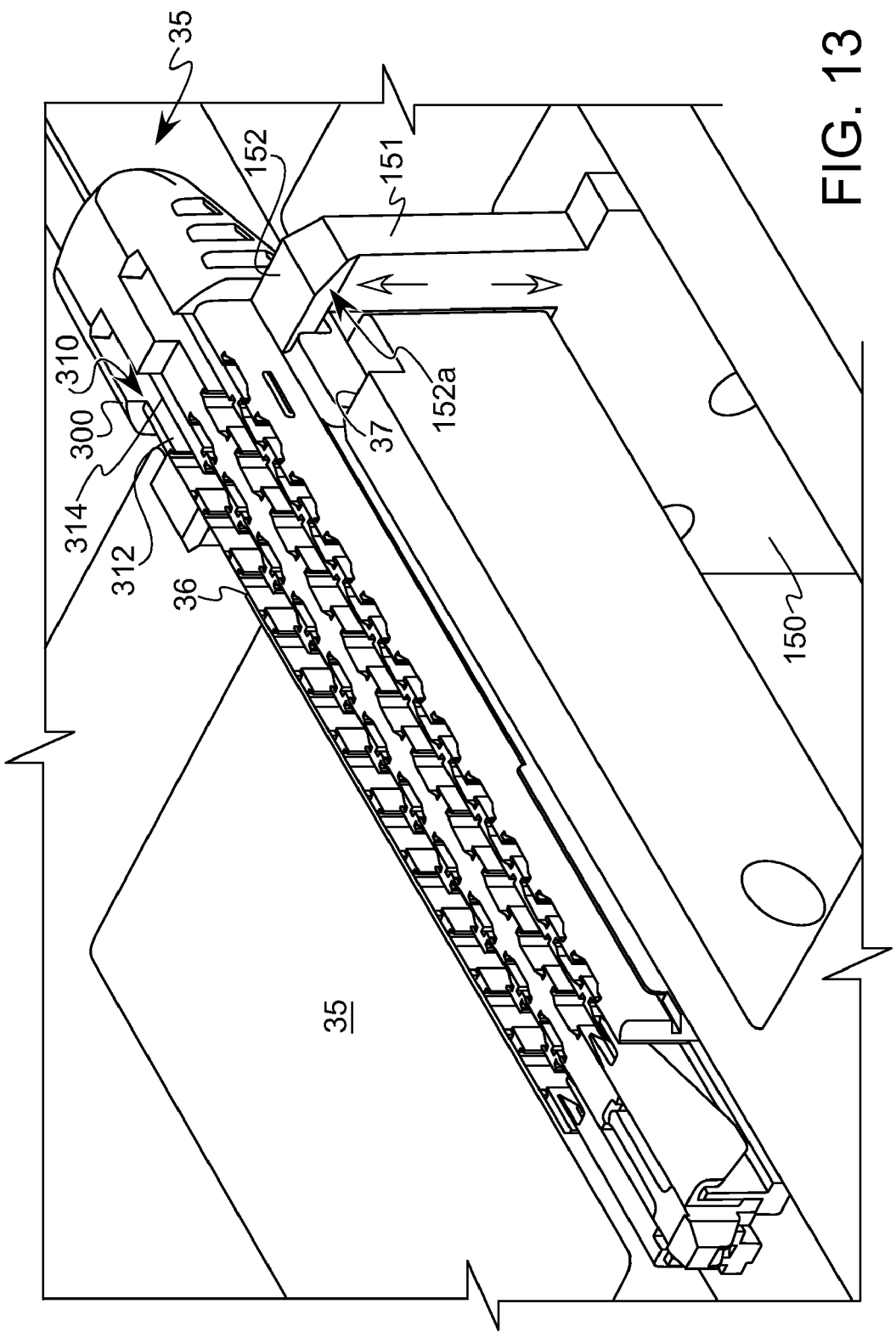
FIG. 13 is a view in perspective illustrating a portion of the present invention with a cartridge in an operable position.

A cartridge-receiving plate 30 is mounted to the base 12. The cartridge-receiving plate 30 has a channel 35 formed longitudinally in a major surface thereof, preferably the surface that faces upwardly during use. The channel 35 is defined by two sidewalls 35a and 35b and a floor 35c (see FIG. 2), against which a cartridge 300 seats for guidance during insertion, and for stability once inserted, into the machine 10 as shown in FIG. 13. Two stops 36 and 37 are formed near one end of the channel 35 for surfaces of the cartridge to seat against as described below.

Figure 3:
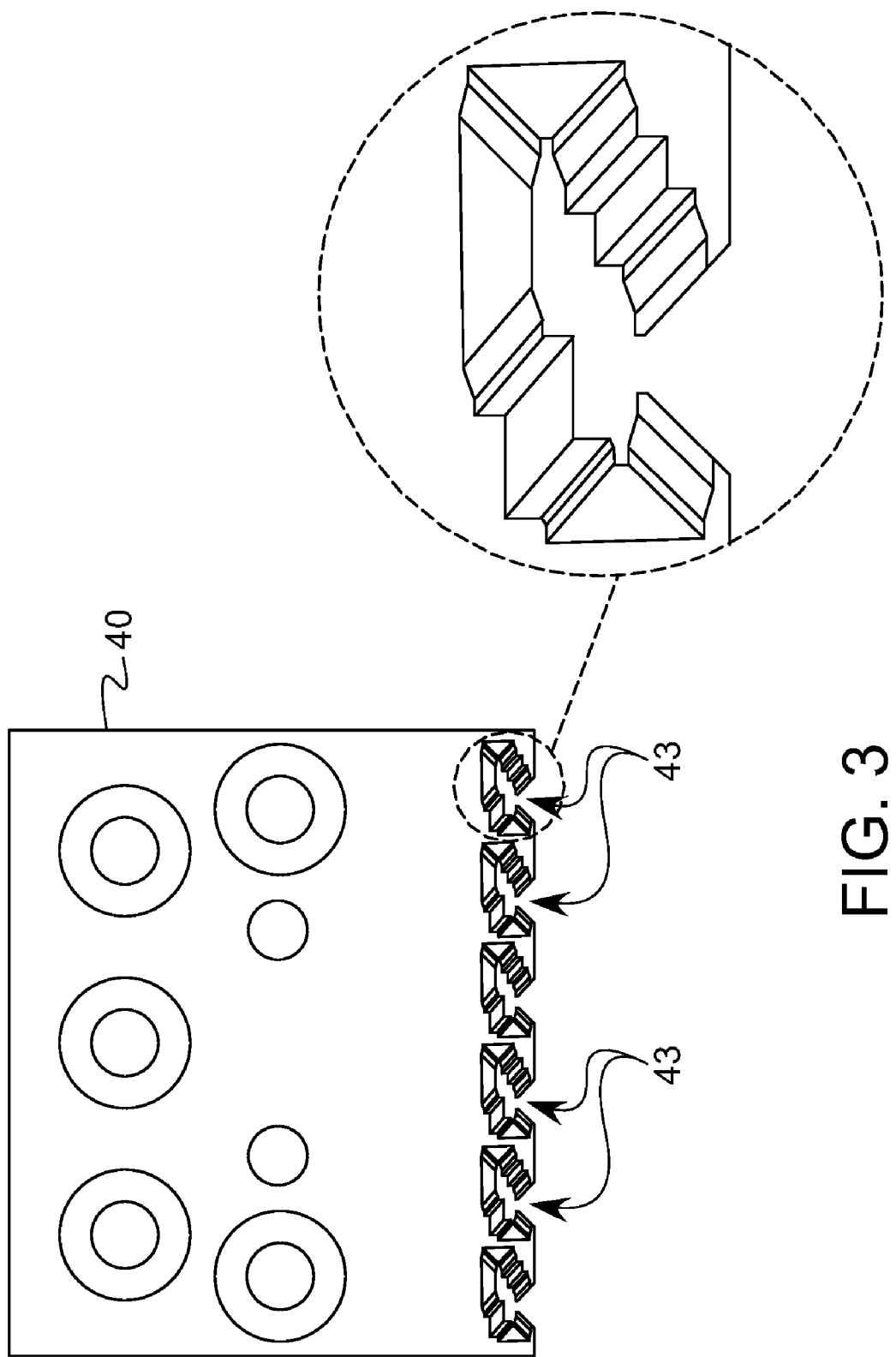
FIG. 3 is a top view illustrating a preferred upper degating plate of the present invention.
Figure 4:
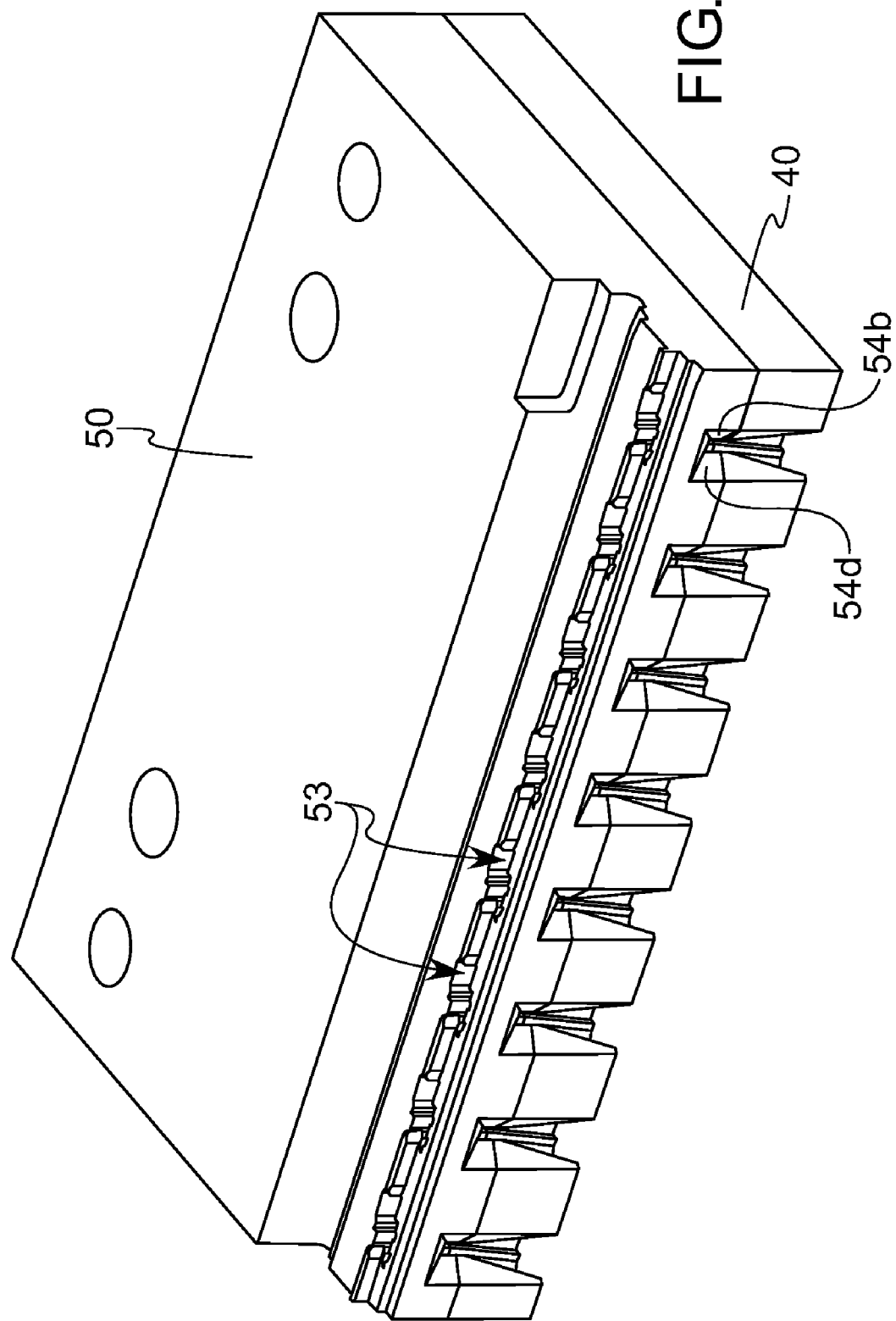
FIG. 4 is a view in perspective illustrating the driver guide fixture, which is the combined upper and lower degating plate.

A driver guide fixture, such as the combination of the upper degating plate 40 and the lower degating plate 50 shown in FIGS. 3 and 4, respectively, is mounted to the base 12 and extends upwardly through the opening 38 in the plate 30, leaving clearance gaps between the upper and lower degating plates 40 and 50 and the plate 30.

The upper degating plate 40 has a plurality of apertures 43 formed therein, extending entirely through the plate 40. The apertures 43 have tapered, converging sidewalls, which create a "funnel effect" to guide drivers inserted therein from the wider openings at the top of the plate 40 to the narrower openings at the bottom of the plate 40. The apertures 43 form a portion of the passage through the degating plates 40 and 50.

The lower degating plate 50 has apertures 53 that extend entirely through the plate 50, the upper ends of which align precisely with the lower ends of the apertures 43 in the upper degating plate 40 when fastened in an operable position to the lower degating plate 40 as shown in FIG. 4. The apertures 53 preferably have non-tapered sidewalls that are aligned precisely with the sidewalls of the pockets of the cartridge 300 positioned in the machine 10. Furthermore, the sidewalls of the apertures 53 very precisely match the outer surfaces of the drivers, thereby preventing any substantial lateral movement of the drivers relative to the lower degating plate 50.

Thus, upon insertion into the apertures 43 of a plurality of drivers fixed on a holder, such as a "tree with branches" holder described above, the drivers are guided toward positions aligned precisely with the apertures 53. Upon further insertion, such as by the plungers described below, the drivers are aligned precisely in the apertures 53 to be mounted in the pockets of the cartridge 300.

Figure 5:
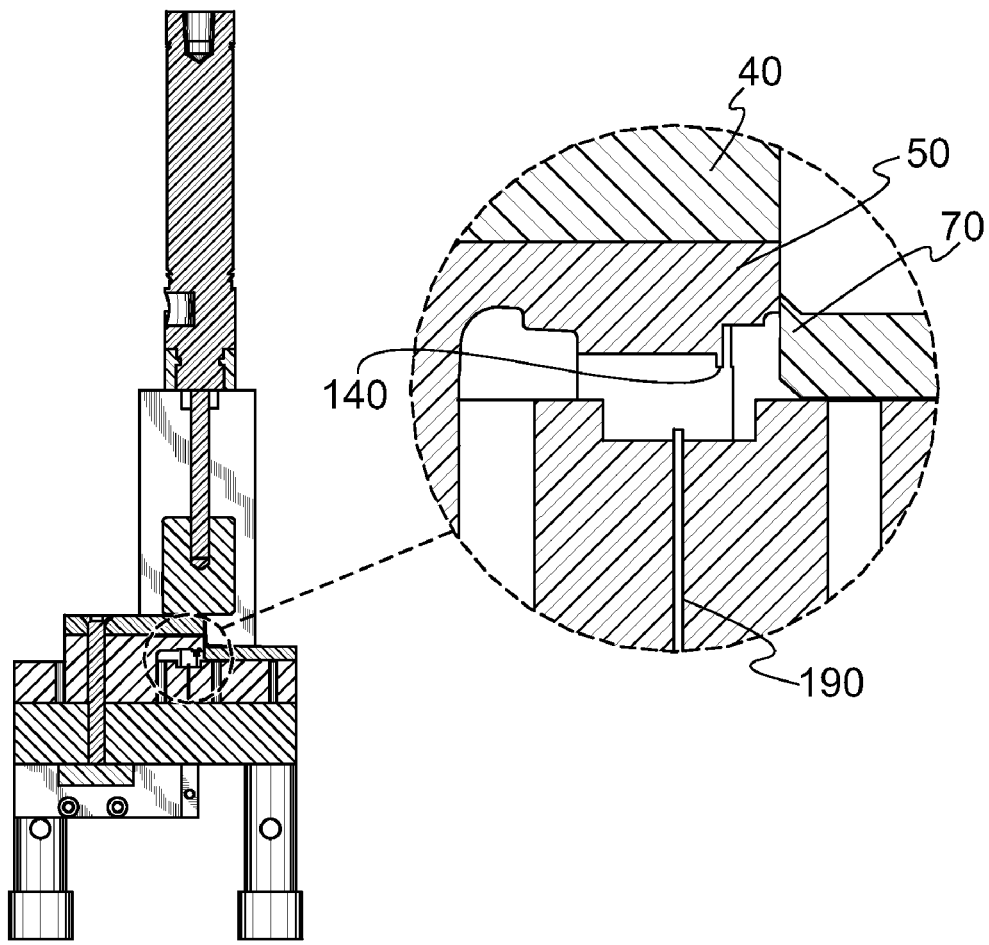
FIG. 5 is an end view in section illustrating the present invention and an enlarged view of the encircled portion of the device.
Figure 6:
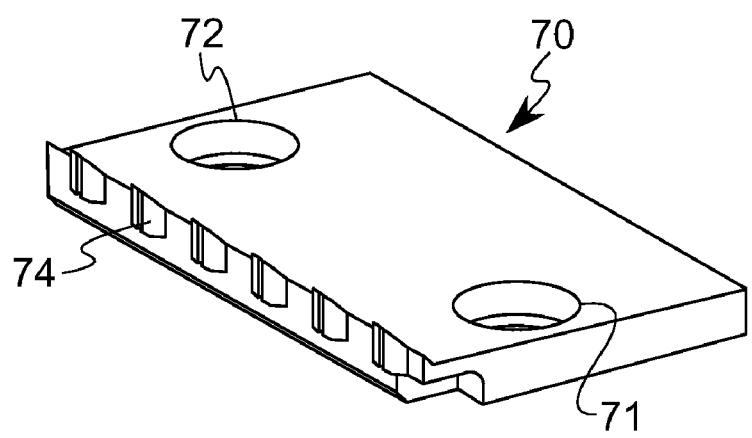
FIG. 6 is a view in perspective illustrating the cutter of the present invention.

A cutter, such as the degating knife 70 shown in FIGS. 5 and 6, is mounted to the base 12. Referring again to FIG. 1, a top riser 80 is adjustably mounted to the base 12. The cylinder arm 90 is rigidly and non-adjustably mounted to the top riser 80. A plunger apparatus, preferably the pneumatic cylinder 100, the guides 110 and 120, the pin holder 130 and the pins 140 (see FIGS. 5, 12, 14 and 15), is mounted to the cylinder arm 90. The pneumatic cylinder 100 functions in a conventional manner to drive the pin holder 130 downwardly along a linear path, as guided by the guides 110 and 120, toward the cartridge-receiving plate 30, and then return the same to a home position. The guides 110 and 120 have bearings and smooth rods to maintain the linear path of the pin holder 130. The bearings provide substantially no resistance to the longitudinal movement of the rods, but substantial resistance to lateral movement of the rods.

Figure 12:
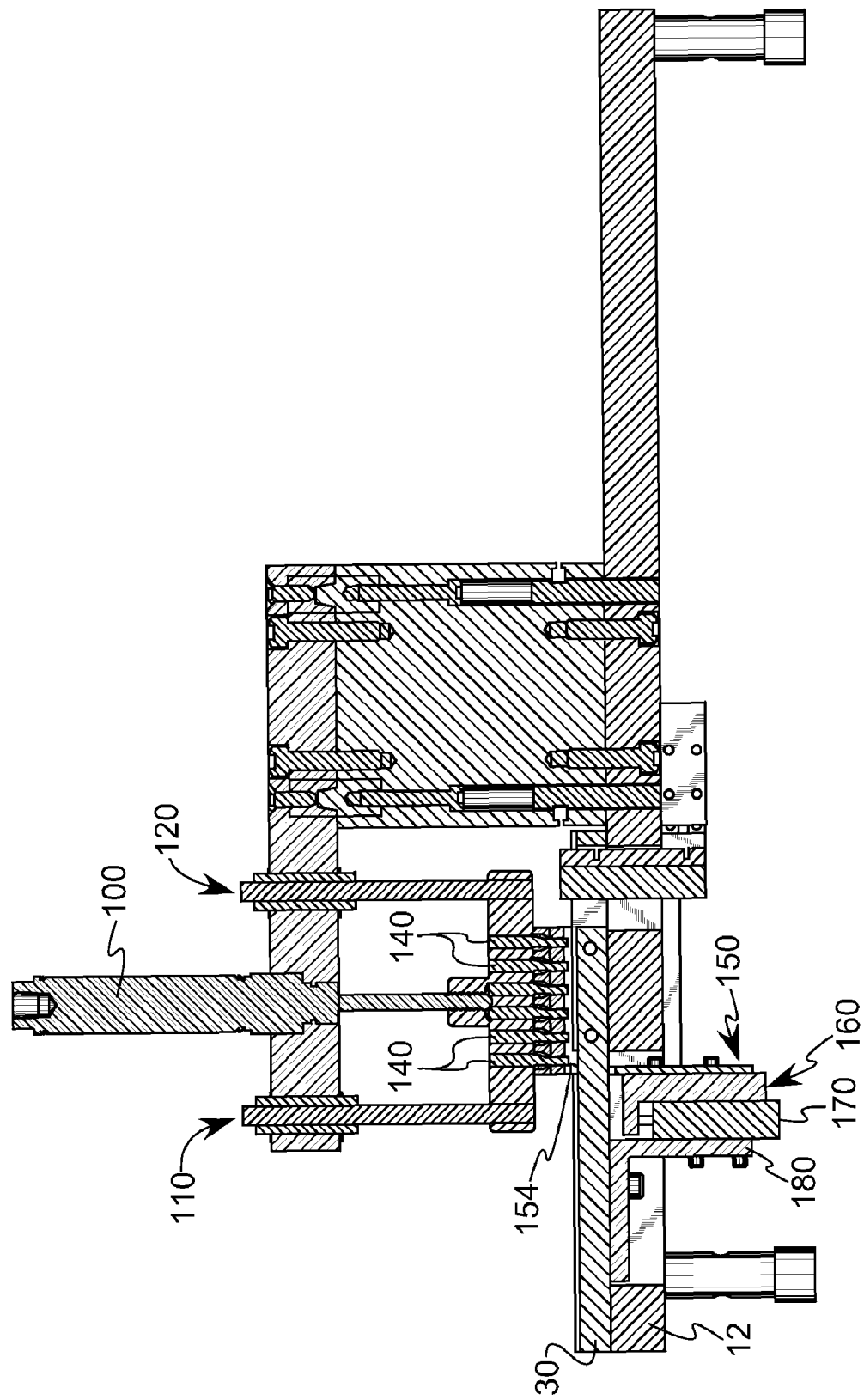
FIG. 12 is a side view illustrating the preferred embodiment of the present invention.

A plurality of pins, such as the pin 140 shown in FIGS. 14 and 15, is mounted to the pin holder 130 aligned to permit the pins 140 to be plunged directly into the apertures 43 and 53 in the degating plates 40 and 50, as shown in FIG. 12. The preferred pins 140 have a tip surface 141 that closely matches the surface of the drivers with which the pin 140 will make contact. Thus, there is a substantially complete contact by the pins 140 with the entire upper surface of the drivers.

The locator plate 150, illustrated in FIGS. 9, 10, 11 and 12, is a substantially planar structure having a pair of legs 151 and 153 that extend from the main body and terminate in tips 152 and 154, respectively. Between the legs 151 and 153 is a gap large enough for the cartridge to be extended through. The tips 152 and 154 have angled faces, such as the face 152a, shown in FIGS. 10 and 13. The tip 154 has a similarly angled face that is not visible in the drawings.

Referring to FIG. 12, the locator plate 150 is mounted to a rigid, L-shaped member 160 that is in contact with the moveable arm of the pneumatic ram 170. The ram 170 is rigidly mounted to a rigid, L-shaped member 180, which is rigidly mounted to the underside, in the orientation shown in FIG. 12, of the cartridge-receiving plate 30. In this configuration, the legs 151 and 153 extend upwardly from the main body of the locator plate 150 through the grooves 251 and 253, respectively, formed in the cartridge-receiving plate 30, as is best viewed in FIGS. 2 and 13.

The tips 152 and 154 extend above the channel 35 in the cartridge-receiving plate 30 as shown in the lowered position in FIGS. 1, 12 and 13. When the locator plate 150 is in its home position, the tips 152 and 154 are significantly above the channel floor 35c from the position shown in FIG. 13, in order for a cartridge to be inserted through the gap between the legs 151 and 153. Once the cartridge 300 is in place, the ram 170 is actuated to displace the locator plate 150 downwardly to the position shown in FIG. 13. This downward force seats the angled face 152a and the angled face on the tip 154 against the end of the cartridge 300, and as the locator plate 150 is displaced downwardly, the "wedge effect" of the angled face forces the cartridge 300 away from the legs 151 and 153, which forces an opposing surface of the cartridge 300 against the stops 36 and 37 as shown in FIG. 13. This locates the cartridge 300 in an exact position, and holds the cartridge 300 in that position during the driver insertion process.

Referring again to FIGS. 2 and 5, a cartridge-locating blade 190 is mounted in the slot 192 formed in the cartridge-receiving plate 30. The cartridge 300 has a longitudinal slot in its underside, into which the blade 190 extends during insertion of the cartridge 300 into the machine 10. The blade 190 thus laterally locates the cartridge 300 during insertion of the cartridge 300 in the channel 35, and laterally restrains the cartridge 300 during insertion of the drivers. It is preferred that the blade 190 only extend a portion of the height of the slot, rather than the entire height, as is conventional, in order to avoid unwanted distortion of the cartridge walls. In one contemplated dimension, the blade 190 extends approximately 0.020 inches into a slot that is at five times that height. It will be understood that other dimensions are possible.

In the preferred embodiment, the pneumatic rams on the machine 10 are connected to a central computer 200, illustrated in FIG. 1. The central computer 200 can be any device capable of logical operations, and is preferably either a single-purpose logic circuit or a multipurpose, programmable microcomputer. Of course, a mechanical computer or any other such device will suffice. The computer 200 is connected to a switch 210, which is depressed by a user of the machine when insertion of the drivers is desired. Sensors are preferably connected to the computer 200 to signal the computer 200 when the rams 100 and 170 are at their extreme positions. These sensors can be internal to the rams, or they can be conventional sensors that permit detection of the position of the moving parts of the rams 100 and 170 and signaling of the computer 200. Examples of such sensors, which the person of ordinary skill will recognize are not the only such devices to be useful, include proximity sensors, optical sensors, mechanical switches, etc.

As shown in FIG. 13, the cartridge 300 has opposing sidewalls 312 and 314 that form boundaries of the pockets into which the drivers are inserted. The pockets are aligned in rows, and the voids that form the pockets align to form the slot 310. The opposing walls 312 and 314 that define the slot 310 and form part of the boundaries of the pockets are joined at their bases (not visible in FIG. 13). The walls 312 and 314 can be displaced relative to one another by bending the walls 312 and 314 and/or the joining material between the bases.

During cooling of the material that forms the cartridge 300, the walls 312 and 314 tend to collapse toward one another (or away from one another), causing the distance between the walls 312 and 314 to be different from the thickness of the driver that will be inserted in the pockets. If the void into which the driver is to be inserted is smaller than the driver, there is the obvious problem that a driver cannot be inserted into a space smaller than it occupies. The invention solves this problem with structures and methods that will now be described.

Figure 16:
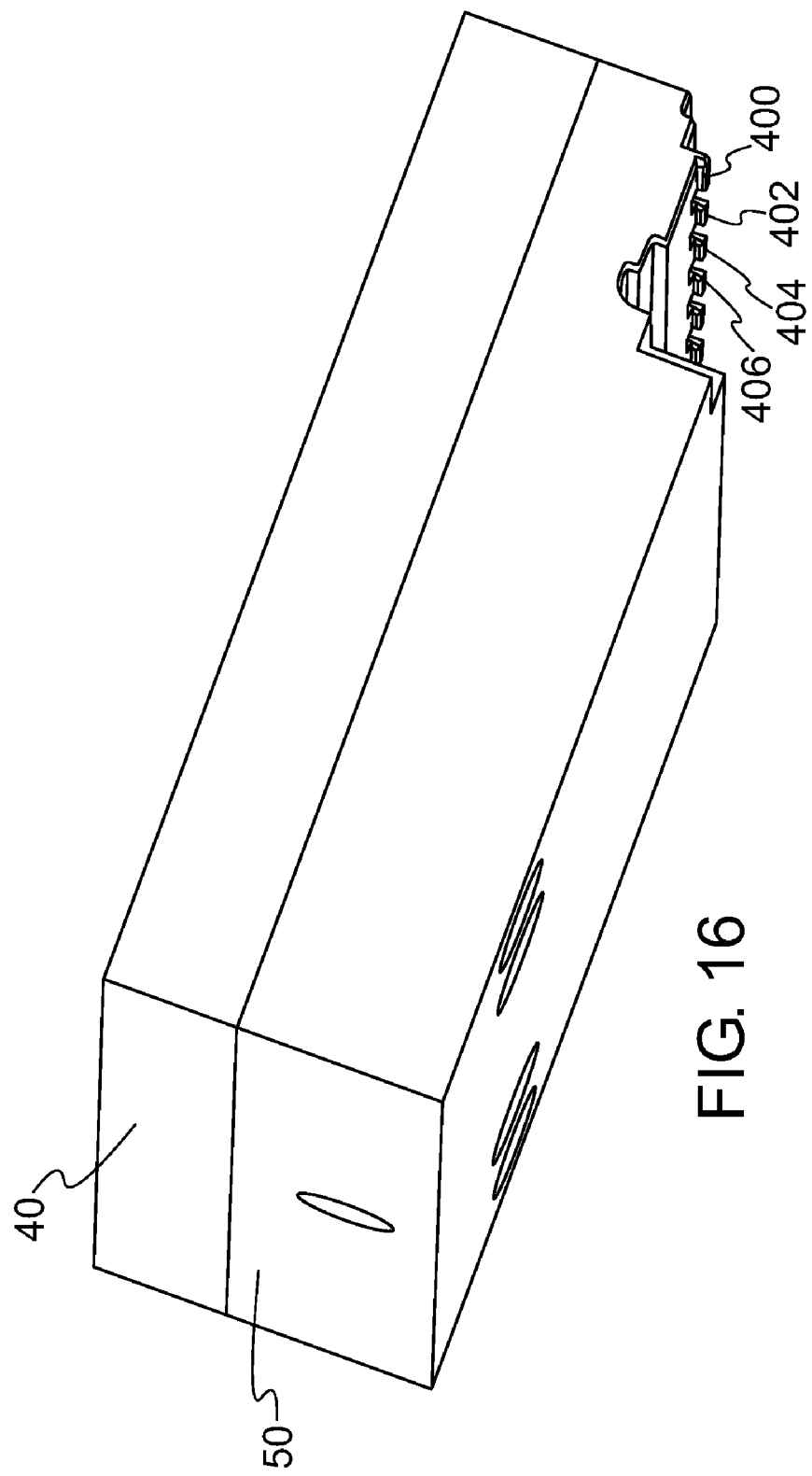
FIG. 16 is a view in perspective illustrating the preferred driver guide fixture.
Figure 17:
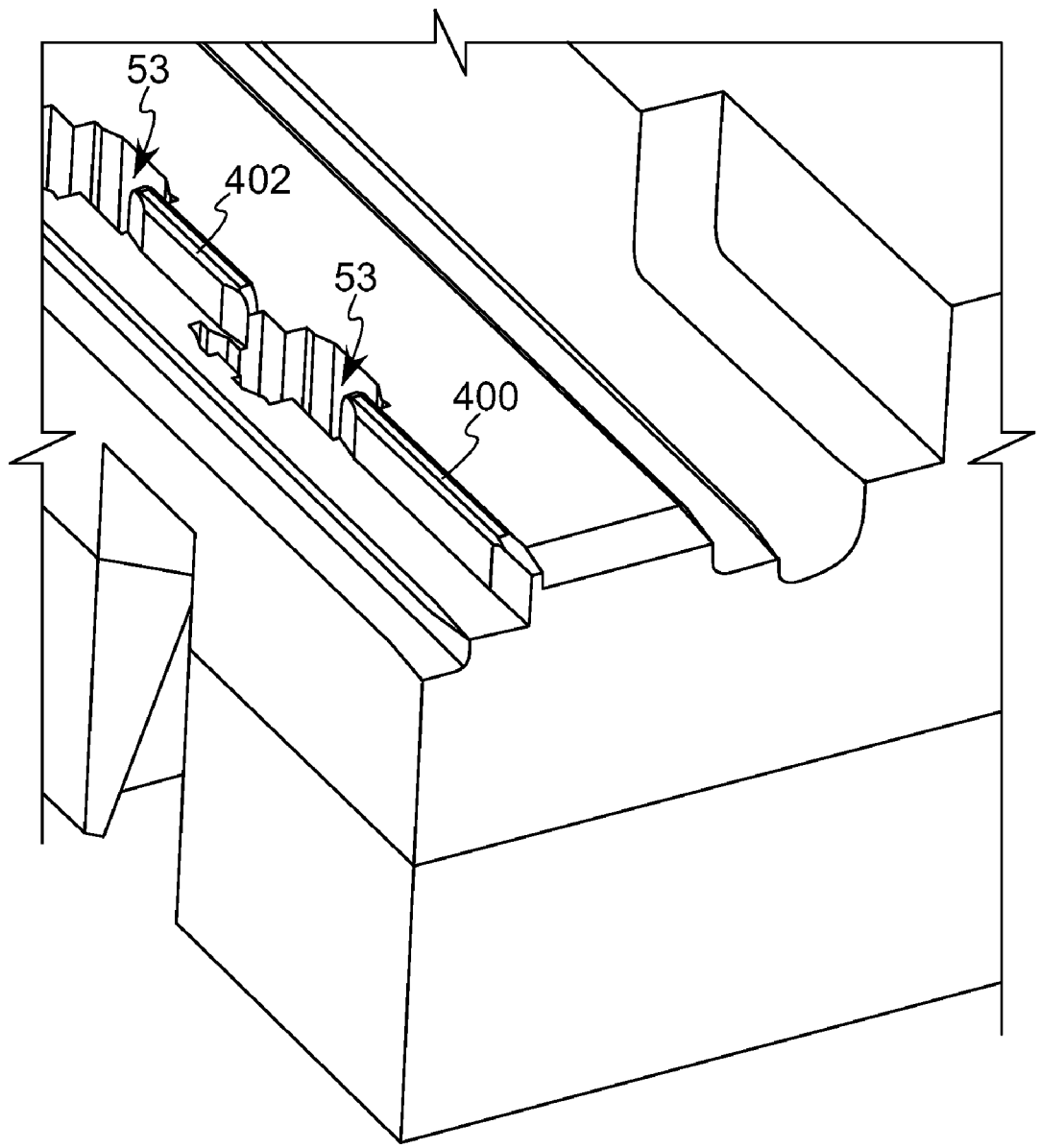
FIG. 17 is an enlarged view in perspective illustrating the preferred lower degating plate fins and apertures.

As illustrated in FIGS. 16 and 17, a plurality of fins 400, 402, 404 and 406 extend downwardly (in the orientation of FIG. 16) from the lower degating plate 50. The fins 400-406 are aligned along a line that is coincident with the apertures 53 so that the fins can extend into the slot 310 (FIG. 13) formed along the top of the cartridge when the cartridge is inserted into the cartridge-filling device. As noted above, during filling of the pockets that align to form the slot 310, the row of pockets in the cartridge is positioned directly adjacent, for example below, the row of apertures 53. This is so that the drivers that are placed in the apertures to align them with the pockets can be driven downwardly exactly into the pockets. By aligning the fins 400-406 with the apertures 53, the fins are precisely positioned in the slot 310 during insertion of the cartridge into the cartridge-filling machine.

Each of the fins is preferably about the same length as each of the spaces between the ends of the apertures 53, or slightly smaller than these spaces, in order not to extend over the edges of the apertures 53, which would cause interference with the drivers driven therethrough. Instead, the fins extend from about the edge of one aperture 53 to about the edge of the next adjacent aperture, as shown in FIG. 17. This forms gaps between the ends of the fins 400-406 that are substantially the same length as the apertures 53, which are substantially the same length as the drivers inserted therein.

Each of the fins 400-406 is preferably shallower than the slot 310 in the cartridge into which it is designed to be inserted. This difference in depth prevents interference with the floor of the slot 310. Additionally, the fins 400-406 are preferably substantially perpendicular to the plane of the lower degating plate 50, as best viewed in FIGS. 5 and 16.

Each of the fins 400-406 is substantially the same thickness. Additionally, the fin thickness is substantially equal to the thickness of the drivers, although the fins can be slightly thicker than the drivers. This substantial similarity in thickness causes the fins 400-406 to cooperate with the walls 312 and 314 when the fins are pushed into the slot 310. The fins move the walls 312 and 314 if the walls 312 and 314 have collapsed toward one another, for example when the molten plastic forming the cartridge cools and hardens. The fins can also move the walls 312 and 314 inwardly as described more fully below in association with the lip. The fins thus dispose the walls 312 and 314 a distance from each other that the resulting slot 310 is substantially equal in width to the drivers. Thus, when the drivers are inserted into the pockets there is essentially no possibility that the walls defining the slot 310 and forming the boundaries of the pockets will be too close together and interfere with the insertion of drivers, even if the walls collapsed during manufacture.

At least one fin is required in the slot 310 to accomplish the task of spreading the cartridge walls apart if they are too close together. It is preferred, however, to have a plurality of fins in the slot 310, and position one fin in every other cartridge pocket during filling of the pockets in the cartridge slot. Thus, half of the pockets are preferably filled in each slot with each row of fins. Of course, more or fewer than half of the pockets in a slot can be filled with each fin, as will be understood by a person having ordinary skill. For example, one-fourth, one-third, three quarters or any other fraction of all pockets can be filled in each slot.

A gap is positioned between each of the fins that is at least substantially the length of the aperture 53. This preferred embodiment distributes the pocket-sizing force of the fins evenly in the slot adjacent every other pocket of the cartridge, thereby avoiding substantial differences between pocket sizes.

Each of the fins 400-406 has tapered ends (see FIG. 17) to ease insertion into the cartridge slot and removal from the slot. During insertion, the tapered fin ends gradually pry the cartridge walls 312 and 314 apart to insert the thicker central region of each fin between the walls. It is this thicker, central region that is substantially the same thickness as the drivers, whereas the terminal ends of the fins are slightly thinner than the central region due to tapering. During removal of the cartridge, the trailing ends of the fins perform the same function: to ease sliding of the fins between the walls 312 and 314. By tapering the leading and trailing ends of each fin, the fins avoid being incapable of entering, or exiting, the cartridge slot.

As noted above, each cartridge has one or more slots formed by the aligned pockets. The lower degating plate 50 shown in FIG. 16 is used for insertion of half of the drivers in the slot 310 of a particular cartridge 300. Because the degating plate 50 is used during insertion of half of the drivers (preferably alternating drivers, which is also referred to as "every other" driver) in the slot of the cartridge, another degating plate must be used to insert the other half of the drivers in the pockets of that same slot. Thus, different degating plates will have different fin and gap configurations in order to insert the drivers in a particular slot. There will be a different lower degating plate, with a different set of fins, for each slot in that particular cartridge 300. For example, if a cartridge has four slots of aligned pockets, and each degating plate is used to insert half of the drivers in the pockets of a slot, one will need eight different degating plates for inserting the drivers for that cartridge. Not all of those degating plates need to be illustrated and discussed herein, because a person having ordinary skill will understand the differences necessary to accomplish the purposes of the invention.

The fins 400-406 are spaced apart so that the gaps between them are adjacent alternating apertures 53. This permits drivers to be inserted within half of the pockets in each row on a cartridge by a first machine with one degating plate. Then the pockets in that row that do not have fins therein are filled with drivers by a second machine. The fins of this second machine's degating plate are disposed in the same row in the cartridge in which the fins 400-406 were previously disposed, but are aligned in the pockets that were just filled with gaps therebetween being aligned in the empty pockets in order to permit filling of the empty pockets that were previously blocked by the fins 400-406.

Thus, the fins 400-406, and substantially similar but differently positioned fins on other degating plates, are used to maintain the walls defining the pockets at a predetermined distance during filling of the adjacent pockets. This prevents any collapsing of the walls, which might have occurred during forming of the cartridge, from interfering with the filling of the pockets with drivers.

Figure 18:
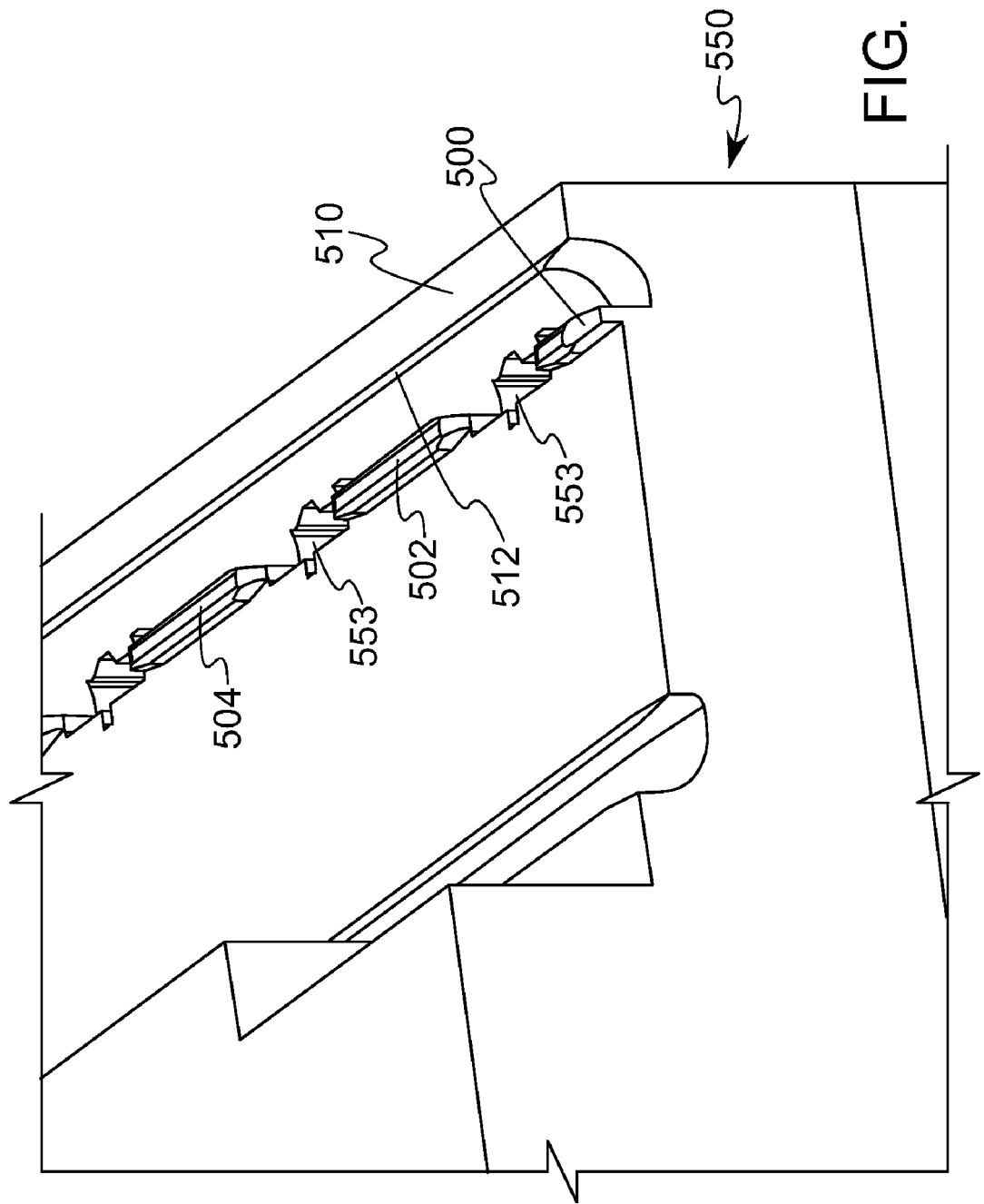
FIG. 18 is an enlarged view in perspective illustrating a different lower degating plate with fins and apertures.

An example of another lower degating plate formed in accordance with the present invention is shown in FIG. 18. The fins 500, 502 and 504 are formed on the top (in the orientation of FIG. 18) of the lower degating plate 550. The fins 500-504 extend to the edges of the apertures 553, but could extend to just short of the edges of the apertures 553. The lip 510 is formed on the lower degating plate 550 to extend over the outer edge of the cartridge in order to form a precisely sized gap between the inner edge 512 of the lip 510 and the outer edges of the fins 500-504. This gap is precisely sized to permit the cartridge wall to fit in that gap when the slot into which the fins 500-504 are inserted is the correct width. If the slot is too narrow, the fins 500-504 spread the walls thereof and correct the width. If the slot is too wide, the lip 510 forces the wall back toward the fins 500-504 to correct the width. Thus, it is clear that not only can the invention increase the width of a slot that is too narrow with the lip combined with the fins, but the invention can also, or alternatively, decrease the width of a slot that is too wide.

Figure 19:
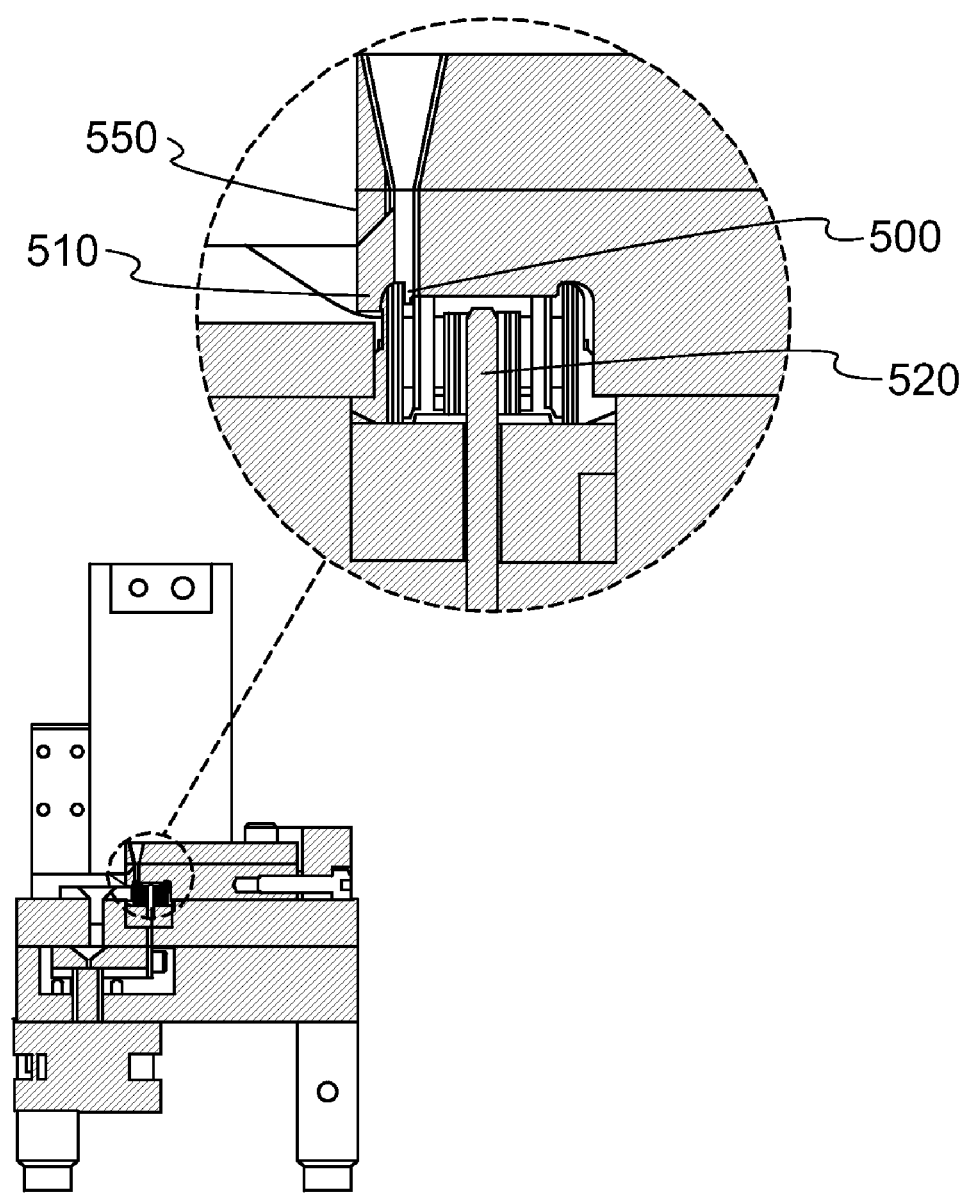
FIG. 19 is an end view in section illustrating the present invention on a device for inserting drivers, with an enlarged section showing detail and the section being made through the fin.

The lip 510 is not the only structure possible to work in association with fins to decrease the width of a slot. It is possible to use a lip 520 as shown in FIG. 19, which lip 520 also operates in the same manner as the locating blade 190 illustrated in FIG. 5. The lip 510 and the lip 520 can both be used to correct the position of walls on opposite sides of a slot, as shown in FIG. 19.

Figure 20:
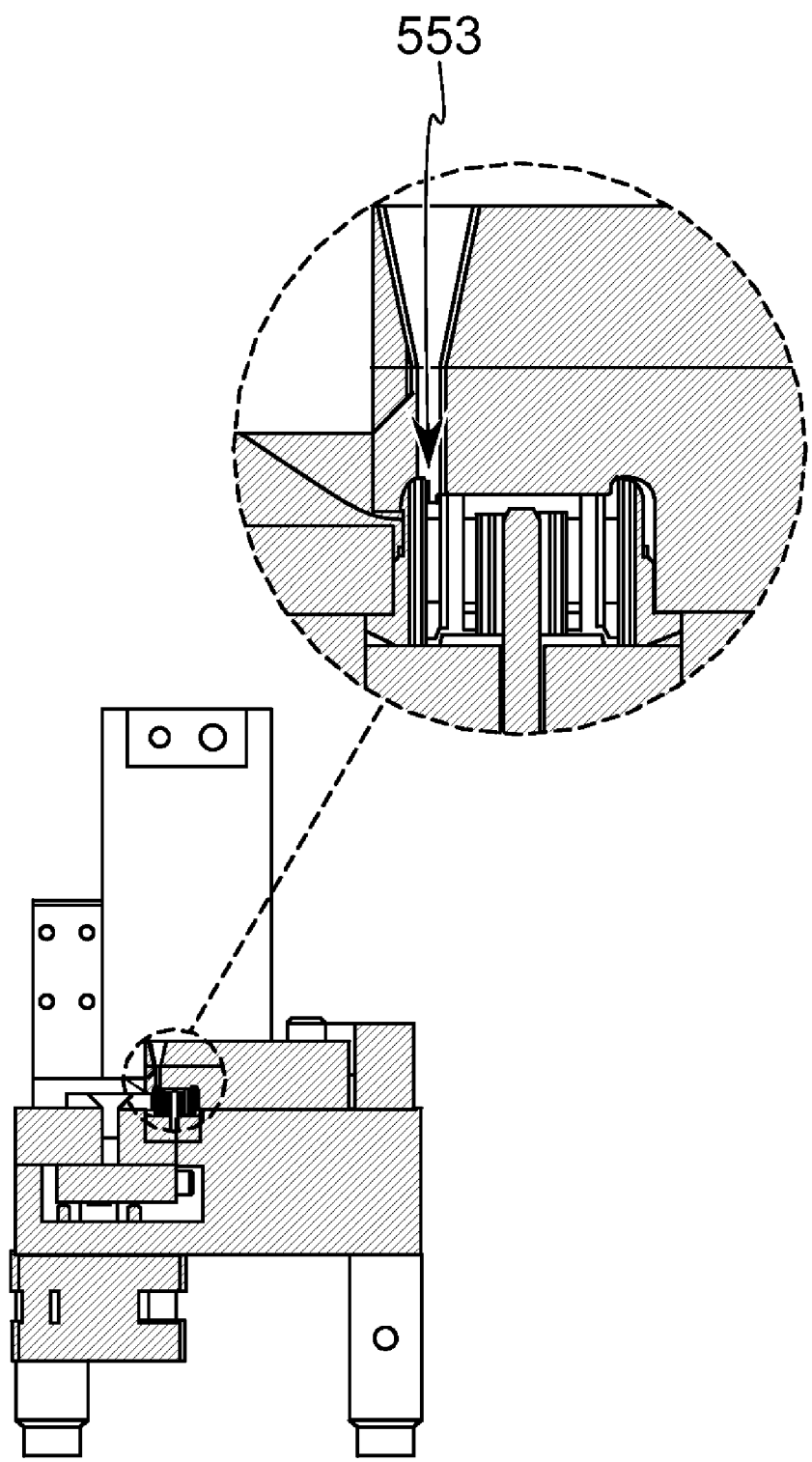
FIG. 20 is an end view in section illustrating the structure of FIG. 19, but with an enlarged section made through the aperture.

The illustration of FIG. 20 aids the person of ordinary skill in understanding how the drivers are inserted through the apertures 553 when the fins 500-504 are positioned in the slot of the cartridge.

The machine 10 operates as follows. A cartridge 300 is inserted into the channel 35 and through the gap between the legs 151 and 153 until the cartridge 300 seats against the stops 36 and 37 with the locator blade 190 in the longitudinal slot of the cartridge as shown in FIG. 13. Before or after the cartridge 300 is inserted in the machine 10, a staple driver holder, with drivers mounted to its tips, is manually placed in the machine 10 with the drivers in the apertures 43 of the upper degating plate 40.

During insertion of the cartridge, the fins 400-406 extend into the slot 310, thereby separating the walls 312 and 314 of the cartridge 300 if the space therebetween is less than the thickness of the fins. If the slot 310 is the correct width, the fins slide between the walls 312 and 314 and gently graze the surfaces of the walls. If the slot 310 is narrower than the correct width, the fins pry the walls apart to make the slot the correct width. If the slot 310 is wider than the correct width, the fins and a lip, such as the lip 510 or 520, push the wall that is, or the walls that are, incorrectly positioned back to the correct position. The leading edge of the lip 510 is tapered, as shown in FIG. 18, in order to ease movement of the cartridge into the space provided between the fins and the lip. The lip 520 is similarly tapered at its leading edge.

Once the walls 312 and 314 are in the correct position, and the slot 310 has the desired width, the drivers are inserted therein by the prime mover 100 driving the pins 140 downwardly into the apertures 43 and 53 to displace the drivers and insert them into every other pocket in the cartridge. The machine is actuated, such as by depressing the mechanical switch 210, which signals the computer 200 to begin the driver insertion process. The computer 200 first actuates the pneumatic ram 170 to draw the locator plate 150 downward, thereby locating and holding the cartridge 300 against the stops 36 and 37 as shown in FIG. 13. Once the locator plate 150 has been displaced downward to its cartridge-locating position, as detected by a sensor as described above, the computer 200 actuates the ram 100 to displace the pin holder 130 and the pins 140 mounted thereon downwardly toward the cartridge 300. While plunging downwardly, the pins 140, which are aligned with the passages in the degating plates 40 and 50, and the pockets in the cartridge, drive the drivers downwardly until the holders contact and pass further by the sharp edges 74a of the knife 70. This motion severs the drivers from the holder and permits the pins 140 to plunge the drivers down further in the passages and into the pockets of the cartridge 300.

Upon reaching the lower extreme of its cycle (shown in FIGS. 1, 5 and 12) as sensed by a sensor as described above, the computer 200 actuates the ram 100 to return the pin holder 130 and attached pins 140 to their home position. Once the ram 100 reaches its home position, or possibly before, the computer 200 actuates the ram 170 to displace the locator plate 150 upwardly, which permits the cartridge 300 to be removed from the channel 35. In a preferred embodiment, a conventional ejector (not shown) is used to eject the cartridge 300 from the channel 35. The cartridge is then placed in another channel on another machine with a different lower degating plate that inserts drivers into the unfilled pockets in the same slot 310. This process is repeated for each slot in the cartridge until the pockets are filled with drivers.

Figure 21:
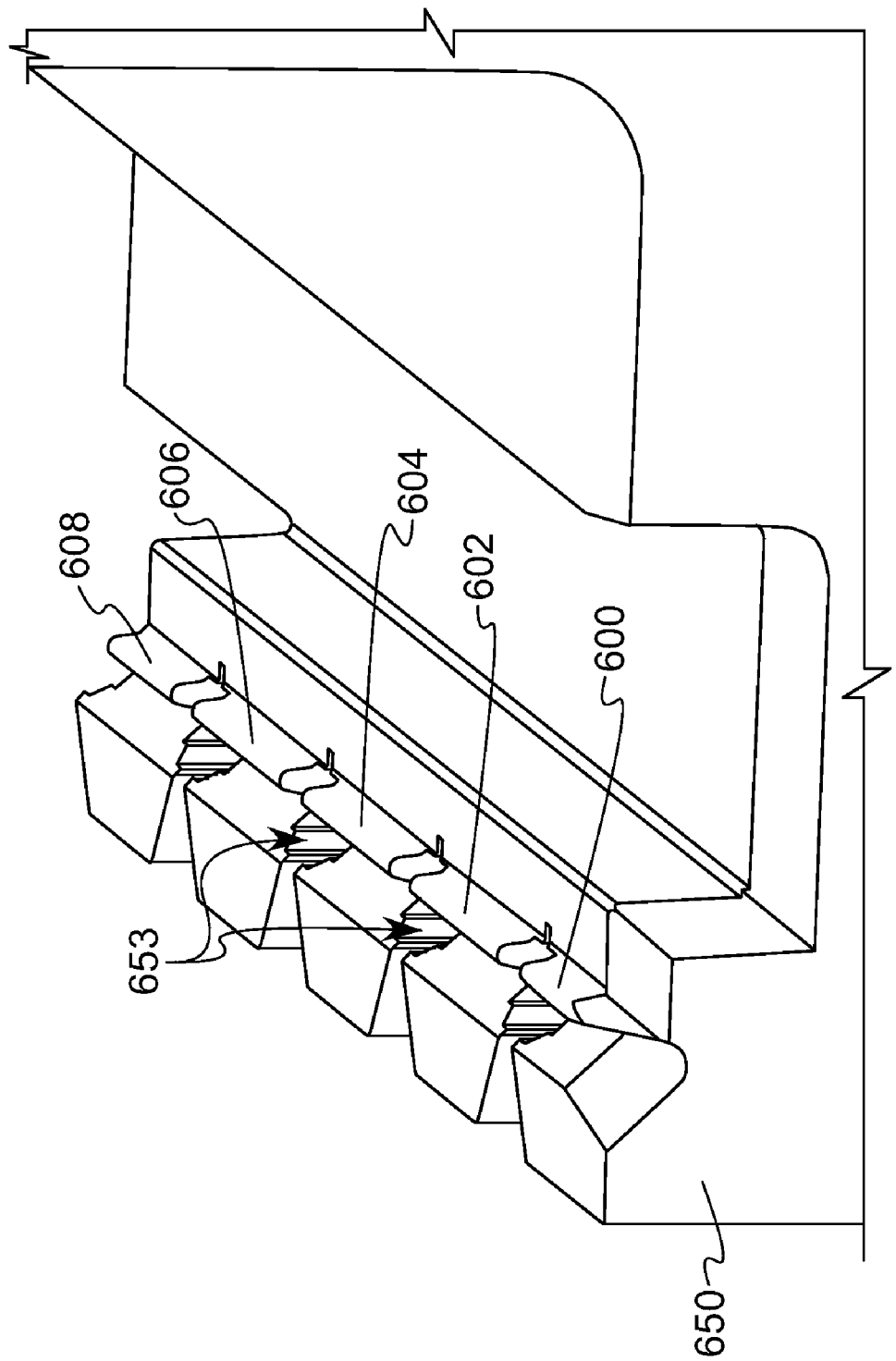
FIG. 21 is a view in perspective illustrating an alternative embodiment of the present invention.

In the preferred embodiment of the invention, the fins are inserted in the slot when the cartridge is inserted in the machine. The cartridge slot is aligned with the fins, and then the cartridge is displaced relative to the machine to insert the fins in the slot. In an alternative embodiment, the cartridge is kept stationary while the fins are inserted into the slot. A lower degating plate 650 is illustrated in FIG. 21 having a plurality of fins 600, 602, 604, 606 and 608. The lower degating plate 650 is displaced relative to a cartridge (not shown) by displacing the fins in a direction parallel to the plane of the fins, and perpendicular to the plane of the degating plate 650 until the fins are within the slot. In this manner, the slots are widened to the desired thickness by the fins.

The fins 600-608 have a similar configuration to the fins 400-406 and 500-504, and a similar relationship to the apertures 653, but are different in some ways. For example, the fins 600-608 are tapered on their leading edges, which are the long edge of the fin, rather than the short ends of the fins as with the fins 400-406. This permits the leading edge of the fins 600-608 to enter the slot from above, rather than the end, as described in association with the fins 400-406.

While certain preferred embodiments of the present invention have been disclosed in detail, it is to be understood that various modifications may be adopted without departing from the spirit of the invention or scope of the following claims.

The invention claimed is:

1. A method of sizing pockets in a surgical staple cartridge and inserting at least one staple driver into one of the pockets that are aligned on the cartridge to form a slot, the method comprising:
   (a) aligning the cartridge with a channel formed in a cartridge-receiving plate below a driver guide fixture having a fixture passage aligned with one of said pockets to receive and guide said at least one staple driver into the pocket;
   (b) displacing the cartridge into the channel, thereby inserting a first fin extending downwardly from the driver guide fixture adjacent the fixture passage into the slot; and
   (c) displacing a plunger aligned with the fixture passage for forcing the driver through the fixture passage and into the pocket.

2. The method in accordance with claim 1, further comprising disposing a lip extending downwardly from the driver guide fixture against a wall defining at least one side of the slot for adjusting the position of the wall.

3. A method of sizing pockets in a surgical staple cartridge and inserting at least one staple driver into one of the pockets that are aligned on the cartridge to form a slot, the method comprising:
   (a) aligning the cartridge with a channel formed in a cartridge-receiving plate below a driver guide fixture having a fixture passage aligned with one of said pockets to receive and guide said at least one staple driver into the pocket;
   (b) displacing the cartridge into the channel;
   (c) inserting into the slot a first fin that protrudes downwardly from the driver guide fixture adjacent the fixture passage; and
   (d) displacing a plunger aligned with the fixture passage for forcing the driver through the fixture passage and into the pocket.

4. The method in accordance with claim 3, further comprising displacing a lip that protrudes downwardly from the driver guide fixture against a wall defining at least one side of the slot for adjusting the position of the wall.

* * * * *